United States Patent [19]

Janko

[11] Patent Number: 4,597,391

[45] Date of Patent: Jul. 1, 1986

[54] OBSTETRIC TRACTIVE DEVICE

[76] Inventor: Albert B. Janko, 977 Pacific St., Monterey, Calif. 93940

[21] Appl. No.: 780,445

[22] Filed: Sep. 26, 1985

[51] Int. Cl.⁴ ............................................. A61B 17/42
[52] U.S. Cl. ..................................... 128/361; 128/352
[58] Field of Search ................................ 128/352, 361

[56] References Cited

U.S. PATENT DOCUMENTS

| | | | |
|---|---|---|---|
| 13,453 | 8/1855 | Buffum | 128/352 |
| 497,720 | 5/1893 | Jones | 128/352 |
| 713,166 | 11/1902 | St. Cyr | 128/352 |
| 1,690,942 | 11/1928 | Odell | 128/361 |
| 1,782,814 | 11/1930 | Froehlich | 128/352 |
| 2,194,989 | 3/1940 | Torpin | 128/352 |
| 2,227,673 | 1/1941 | Price | 128/352 |
| 2,792,838 | 5/1957 | Guerriero | 128/352 |
| 3,592,198 | 7/1971 | Evans | 128/352 |
| 3,765,408 | 10/1973 | Kawai | 128/352 |
| 3,794,044 | 2/1974 | Vennard et al. | 128/352 |

FOREIGN PATENT DOCUMENTS

| | | | |
|---|---|---|---|
| 2233840 | 1/1974 | Fed. Rep. of Germany | 128/361 |
| 2925386 | 1/1981 | Fed. Rep. of Germany | 128/361 |

OTHER PUBLICATIONS

German Congress of Perinatal Medicine, vol. IV, Nov. 1-5, 1972, article by E. Saling.

*Primary Examiner*—Gene Mancene
*Assistant Examiner*—David I. Tarnoff
*Attorney, Agent, or Firm*—Wood, Herron & Evans

[57] ABSTRACT

An obstetric device for the tractive delivery of a fetus is disclosed. The delivery device comprises a tractive net which includes a set of spaced apart, elongated and pliant structural ribs. A pattern of threads forming a mesh is carried and supported by and between the ribs. The net is designed to be introduced into the birth canal in a folded condition, opened to surround the circumference of the fetal head, or calvarium, and then fixed in position. A simple fastening mechanism is carried on two end ribs to close the net. The now tubular-shaped net can be firmly grasped at one end and pulled to tractively orient and/or deliver the fetus. The threads composing the net are specifically designed to tear or rupture at a predetermined limiting or maximum tension, so as to prevent injury to the fetus in the event that excessive pulling force is used.

6 Claims, 6 Drawing Figures

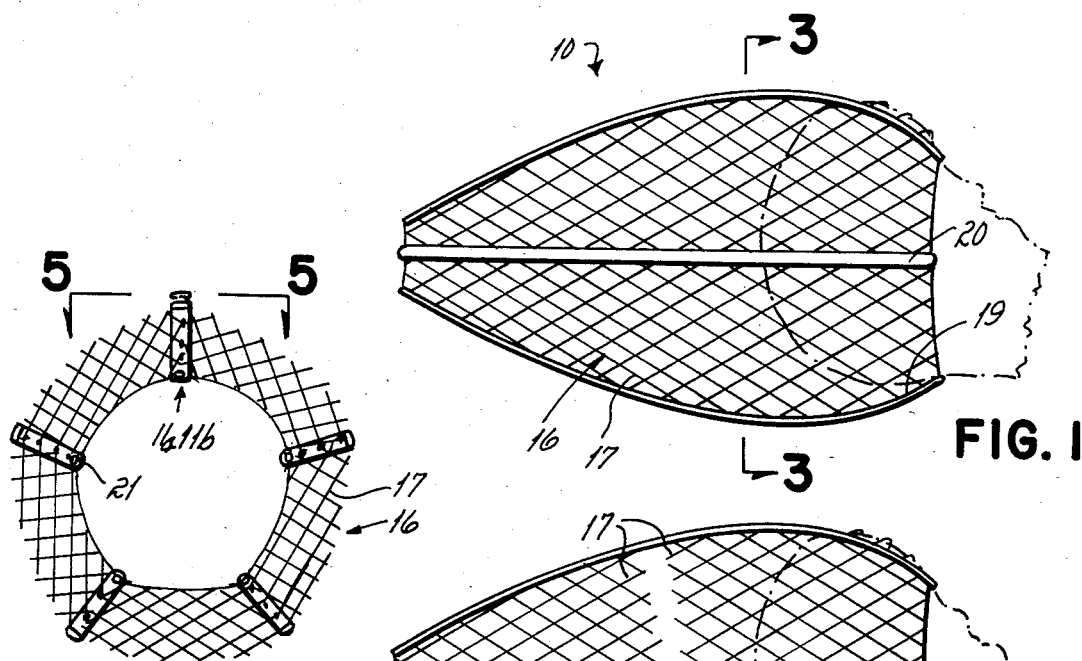
FIG. 1
FIG. 2
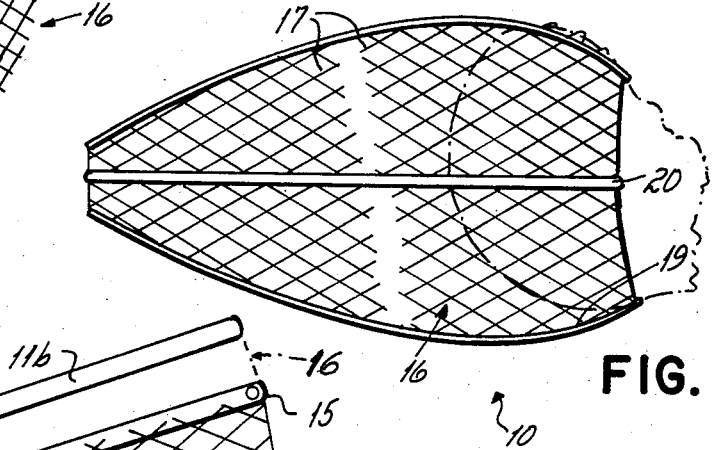
FIG. 3
FIG. 5
FIG. 6
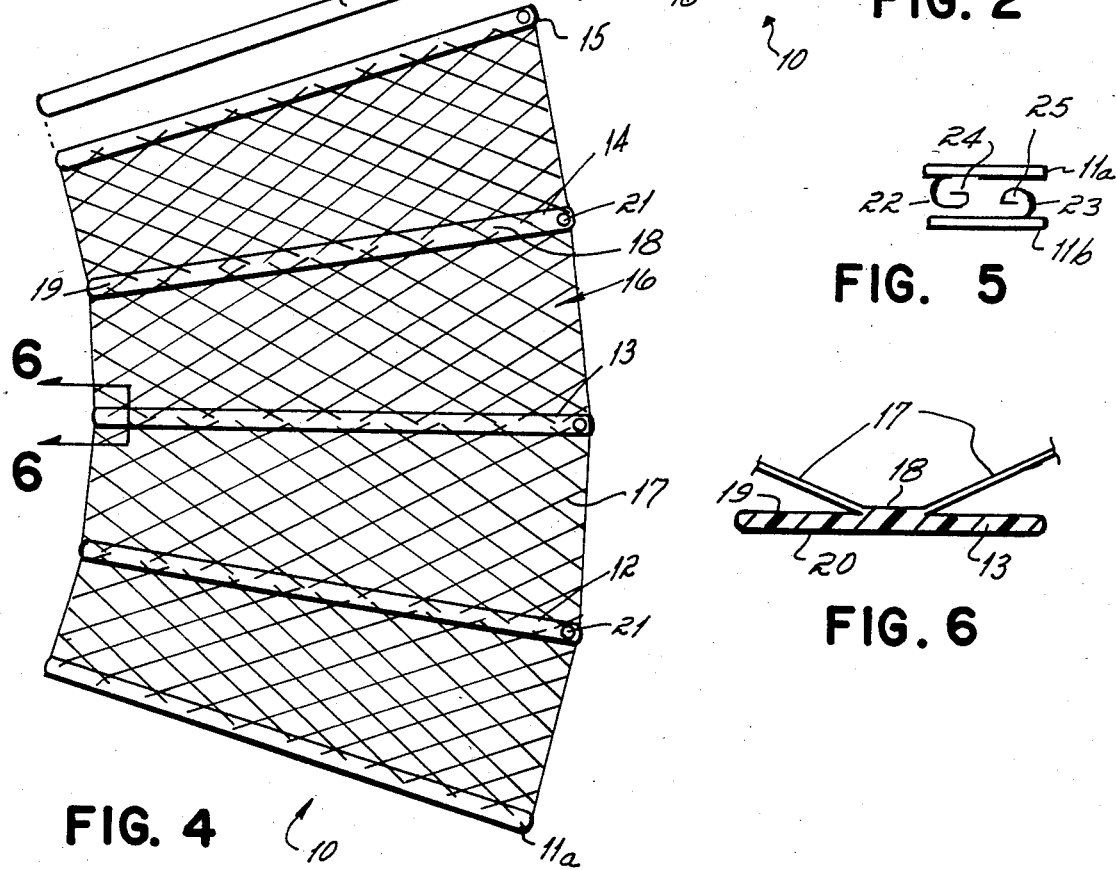
FIG. 4

OBSTETRIC TRACTIVE DEVICE

FIELD OF THE INVENTION

This invention relates generally to tractive obstetric delivery devices, such as forceps, and more particularly to a flexible, tractive delivery net which is placed around the head of the fetus in utero to form a tubular shape which can be grasped at one end and gradually drawn to deliver the baby.

BACKGROUND OF THE INVENTION

Obstetrical forceps are almost universally used where it becomes necessary to apply tractive force to the fetus during childbirth. Heretofore, nearly all obstetrical forceps were manufacturing from unyielding materials, such as stainless steel. When such rigid material is engaged against the soft, moldable fetal head, undesirable and potentially damaging compression can occur. This, of course, is an inherent drawback in the use of such forceps, and the avoidance of the inherent dangers associated with use of forceps on the fetal head has been a matter of constant concern. A faulty application or incorrect use of the forceps will not only injure the fetus, but can also cause maternal injuries as well. Since present day obstetrical training programs tend to deemphasize the use of forceps, it can no longer be assumed that those who infrequently use forceps will be thoroughly proficient in their use, increasing the danger that either fetal or maternal injuries are likely to follow.

Investigations have clinically and experimentally measured the compression and tractive forces applied in the use of obstetrical forceps. An average compression force on the fetus' skull of 20 kg. has been generally observed as being the approximate threshold level of force below which forceps would not likely produce injuries to the fetus, while above which injury was likely to occur. In general, the average compressional force applied to primigravidas was approximately 18 kg., and in multi-pares 13 kg. The delivery pressure of the uterine muscles was recorded at 4.2 kg., increasing to around 9 kg. with expulsive efforts.

Faulty application of the forceps can result in elevation of the tentorium and displacement of the faix, which can become excessive with tear, and can be followed by subcortical and cortical bleeding or sinus rupture. The sagittal sinus can also end up congested and dilated, and the brain stem angulated. It has been observed that fetal electroencephalograms show rapid change from low voltage to irregular activity to even flat line recordings after forceps application. Such irregular activity was not seen in spontaneous deliveries. Further, fetal heart rate was found to vary in relation to the fetal head compression.

Initial application of the forceps is usually for the purpose of converting an unfavorable presentation to a more favorable one by rotating the fetus in the birth canal. Once in a proper presentation, the forceps are then used to apply tractive force to the fetal head and thereby assist in delivery by effectively pulling the infant through the birth canal.

Besides the already noted problems related to unyielding compression of the fetal head, forceps also are subject to friction between the outer surface of the forceps and the birth canal, which adds to the tractive forces which must be applied for successful delivery.

The concept of using a constricting net for tractive delivery of a fetus is not new in the art, as shown by U.S. Pat. No. 13,453 and 713,166. Both of these patents show a resilient net or web which is placed around the fetal head in utero through the use of rigid blade members. Once in place surrounding the fetal head, the free net end can be grasped and pulled to effect rotation and/or delivery. Such tractive nets have the advantage that the compression force applied to the fetal head is more evenly distributed.

As will be more clearly shown in relation to the instant invention, both of the foregoing nets disadvantageously employ rigid blades to position the net, and neither net features a mesh which ruptures at a predetermined excessive force.

SUMMARY OF THE INVENTION

It was in view of the problems attendant upon the use of forceps that the instant invention in an obstetrical tractive net for use in childbirth was devised. One object of the net is, of course, to provide an improved obstetrical tractive device. Another object of the invention is to provide an improved obstetrical tractive device which decreases the chances of fetal injury and provides a satisfactory means for rotation and/or delivery of the fetal head.

Yet another object of the invention is to provide a pliant tractive net which surrounds the fetus' head in utero and provides a relatively uniform compressive force thereabout which helps to mold the head to conform to the passageway of the birth canal. Still another object is to provide such a tractive net which can be easily inserted and fixed in place around the fetal head in utero, and which can be successfully used even by those with little or no experience with the device.

Yet another object of the invention is to provide a tractive net which firmly grips the fetal skull for secure manipulation thereof, but creates minimal fiction between the birth canal and the delivery net.

The most significant object of the invention is the provision of an obstetric tractive net which is designed to tear or rupture upon the application of tension, or pulling force, which exceeds a predetermined threshold level, to thereby prevent or substantially decrease the risk of fetal injury in tractive delivery.

These and other objects are accomplished in an obstetric delivery device comprising a tractive net having spaced apart, elongated and pliant structural ribs which carry a flexible strand. The net, in open planar condition, is in a form much like a fan shape, with the ribs representing the structural rib portions of the fan and the thread mesh the main portion of the fan body.

The tractive net is folded (like a fan) for insertion into the uterus, or birth canal, and then manipulated therein by the fingers to wrap laterally around the fetal head to thereby form a columnar-shaped tube which partly extends out of the uterus. The two outermost or end ribs come together to form this tube, and carry mating portions of a fastener which can be secured to hold the net in tubular form. Once in place, the free end of the tube extending outside the birth canal is grasped by the physician and gently rotated and/or pulled so as to manipulate the fetus' head.

In its preferred form, the net mesh is made in a diamond-shaped pattern, with the long area of the diamonds extending parallel to the ribs. This increases the net's ability to grip the fetal head, since as the net is pulled the diamond-shaped net pattern elongates along the diagonal in the direction of the pulling force, thereby compressing or shrinking the tube radially inwardly, causing the tube to tighten about the fetus' head. Additional gripping of the fetal head is preferably provided by a suction cup pattern which is formed on the side of the structural ribs which engages the fetal head. The outwardly facing surface of the ribs is desirably glassy-smooth so as to minimize friction with the birth canal.

A most significant attribute of the delivery net of this invention is that the net is designed to tear or rupture at a predetermined threshold level of tractive force. For example, given the presumption that injury is likely to occur to the fetus upon the application of compressive forces of 20 kg. or more, the threads forming the net mesh would be designed to break upon the application of tension yielding a compressive force at or in excess of 20 kg. This safeguards against the use of potentially excessive pulling force when employing the delivery net. Additionally, this safety feature adds to the utility and desirability of this obstetric delivery tool, since it ensures that one who has had little experience with the net will be able to use it without the risk of inadvertently applying a potentially damaging force to the fetus. The tractive net of this invention is thus far more forgiving than the present day obstetric forceps when used in the hands of the inexperienced.

The foregoing objects, features and advantages of the present invention will be more readily understood upon consideration of the following detailed description of the invention taken in conjunction with the accompanying drawings in which:

BRIEF DESCRIPTION OF THE DRAWINGS

FIG. 1 is a diagrammatic elevational view showing a tractive net in accordance with a perferred form of this invention, in place around a fetal head;

FIG. 2 is a view similar to FIG. 1, but showing the net torn due to the use of excessive tractive force;

FIG. 3 is a cross-sectional view taken along line 3—3 of FIG. 1 of the net in its closed, tubular shape;

FIG. 4 is a plan view of the open net;

FIG. 5 is a cross-sectional view taken along line 5—5 of FIG. 3 detailing one form of fastening mechanism;

FIG. 6 is a view taken along line 6—6 of FIG. 4 showing one manner of attaching the mesh strands to the ribs.

DETAILED DESCRIPTION OF A PREFERRED EMBODIMENT OF THE INVENTION

The obstetric delivery or tractive net of this invention is shown in a presently preferred form in FIG. 4, and is generally designated by the numeral 10. The net 10 is comprised of a plurality of elongated, thin structural ribs 11a, 11b-15 which carry a mesh 16 thereon, which mesh is composed of resilient threads or strands 17. The outermost or edge ribs 11a and 11b carry fastening means so that the net can be fixed in a tubular shape (FIGS. 1, 2 and 3) by attaching rib 11a to rib 11b in a manner to be described more fully below.

As best shown in FIG. 4, the net 10 is preferably formed in a fan shape with the net widest in the area which will surround the fetal head. The preferred pattern for the net mesh 16 is that of a diamond-shaped pattern. This pattern increases the ability of the net to grip the fetal head with the net in place, as in FIGS. 1 and 2. That is, as the net is grasped about the free end of the tube formed by the net and pulled, the diamond-shaped pattern tends to elongate along the diagonal (the axis parallel to the ribs) in the direction of the pulling force being applied. This causes the mesh to contract along the other diagonal (i.e. perpendicularly to the ribs), causing the net to contract radially inwardly and thus grip the fetus' head more firmly.

The structural ribs 11-15 are made of a pliant material, preferably "Silastic", a silicone rubber, of sufficient rigidity to hold the general pattern of the net. The ribs 11a, 11b-15 are flexible enough to be easily manipulated around the fetal head within the close confines of the birth canal, however. The ribs 11a, 11b-15 are relatively wide but thin, and have flat inner and outer side surfaces 19 and 20, respectively. The outer surface 20 is perferably glassy-smooth to minimize friction between the net and the birth canal. This decreases the chance of maternal injury, as well as minimizes the amount of tractive force which may be required in manipulation and delivery of the fetal head. In this embodiment, the inner surface 19 of the structural ribs 11a, 11b-15 is provided with a number of very small suction cups 21 at least in the area of the net which will be in contact with the fetus' head. These suction cups further increase the grip of the net around the head. This pattern may be advantageously formed on the ribs 11a, 11b-15 at the time the ribs are molded.

The strands 17 forming the mesh 16 are preferably thin plastic threads also formed from "Silastic", for example. The strands 17 form a preferred diamond-shaped pattern mesh 16, with the mesh 16 attached to the structural ribs, as by fusing or adhering at the point of contact between the mesh and the ribs, as shown at 18 in FIG. 6. Other methods of affixing the mesh 16 to the structural ribs 11a, 11b-15 can, of course, be employed.

A presently preferred mechanism for fastening the ribs 11a and 11b of the net together to form the tubular shape for tractive delivery is a simple, overlap seam-type mechanism. Each of the mating members 22, 23 of the mechanism are respectively formed on the outside edges of the end ribs 11a and 11b. This type of fastening mechanism is presently preferred since it can be easily manipulated by the physician. Additional attaching means in the form of compatible co-acting connectors 24, 25 of "Velcro" hook and pile fastener can be provided along the interior of the mating members 22, 23 to ensure that the net ends remain firmly fastened together. Other attaching mechanisms can be employed, such as snaps or pressure sensitive adhesive, to hold the ribs 11a and 11b together.

The most significant feature of the tractive net of this invention is the ability of the net to tear or rupture at a predetermined amount of tensional or pulling force. Should the physician pulling on the net exceed this predetermined level of force (not yet determined numerically, but believed to be in the range of about 15-35 kgs. tractive pull on the device), the strands 17 are designed to rupture, causing the mesh 16 to tear thereby releasing the net 10. This built-in safety factor of a break point for the net thus forces the physician or other user to re-evaluate the situation in light of the obviously excessive force which a tractive delivery may entail. The physician thus is given the opportunity to choose an alternative delivery method or face an increased risk of fetal injury if a vaginal delivery is continued, as by the use of forceps.

In use for delivery, the tractive net 10 is folded closed like a fan. The folded net 10 is then introduced into the birth canal by passing the widest end of the net over the operator's hand and through the posterior forchette to a point where the end of the net has passed beyond the calvarium of the fetus. The net is then opened in situ, first one end rib 11a or 11b being carried with the hand by a sweeping motion around the fetus' skull, and then the other end being carried in a like manner around the other side of the fetal skull. The fastening mechanism 22, 23 carried on the end ribs 11a, 11b is then secured. FIGS. 1 and 3 show the net in position for use.

With the net 10 fastened and in place, the free end of the now tubular-shaped net extending out of the birth canal can then be manipulated to first effect rotation of the fetal head to achieve a more favorable presentation. It will be noted that since the delivery net is made of a pliable, thin material and snuggly fits the fetus' head, it does not have the fixed fetal or pelvic curvatures as well as the thickness of the traditional rigid forceps. This is, of course, of equal advantage compared to the rigid blades used in U.S. Pat. Nos. 13,453 and 713,166, previously discussed. The net of this invention thus is able to conform to the fetus' head with insignificant resistance to the natural contours of the birth canal, thus increasing the ease in converting an unfavorable presentation to a more favorable one.

Following rotation, traction can be applied either directly by the operator grasping the net with a hand and pulling, or by a simple weight and pulley arrangement which would provide a continued, slow traction to take place. In either instance, the ability of the net to rupture at a predetermined level of tension safeguards against use of excessive force, thereby substantially preventing injury to the fetus through tractive delivery.

Thus, while the invention has been described in connection with a certain embodiment, it will be apparent to those skilled in the art that many modifications of structure, arrangement, portions, elements, materials and components can be used in the practice of the invention without departing from the principles of this invention.

What is claimed is:

1. An obstetric delivery device comprising:
   a tractive net, the net composed of spaced apart longitudinal structural ribs carrying a mesh, the net being sized to be wrapped around the circumference of a fetal head in utero, to overlay itself and thereby form a columnar shaped tube for tractive delivery of the fetus,
   means for securing overlaying portions of the net together in situ to hold the net in a tubular configuration around the fetal head,
   the net being adapted to tear at a predetermined limiting level of tractive tension to release the tractive force on the fetus to reduce risk of injury to the fetus during such tractive delivery.

2. A tractive obstetric device comprising:
   a net formed of a frangible material,
   means to secure the net in a generally tubular configuration when one portion of the net is placed around the head of a fetus in utero, such that another portion of the net can be grasped and pulled to effect delivery of the fetus,
   the net when put in traction being adapted to rupture at a predetermined limiting level of tractive tension thereby to lessen the risk of injury to the fetus during such tractive delivery.

3. The obstetric device of claim 2 wherein the net is further comprised of a set of elongated spaced apart ribs, and a resilient mesh carried by the ribs.

4. The obstetric device of claim 3 wherein the mesh is composed of strands in a diamond shaped pattern, the pattern having one axis which is parallel to said ribs.

5. The obstetric device of claim 4 wherein each rib presents one face in contact with the birth canal having a substantially smooth surface, and an opposed face for contact with the fetus and having suction means along at least a portion thereof for reducing slippage of the rib on the fetal head.

6. The obstetric device of claim 3 wherein the means to secure the net in a generally tubular configuration comprises means on at least one rib to connect that rib to an adjacent rib in situ, thereby to connect said ribs to form the net into a tube.

* * * * *